United States Patent [19]
Alzain

[11] Patent Number: 5,104,386
[45] Date of Patent: Apr. 14, 1992

[54] DENTAL SYRINGE APPARATUS

[76] Inventor: Mohammed O. Alzain, P.O. Box 4450, Kingdom of Saudi Arabia, Riyadh, Saudi Arabia

[21] Appl. No.: 685,882

[22] Filed: Apr. 16, 1991

[51] Int. Cl.⁵ .............................................. A61M 5/00
[52] U.S. Cl. .................................. 604/232; 604/198; 604/263
[58] Field of Search ............... 604/232, 198, 263, 187, 604/110, 218

[56] References Cited

U.S. PATENT DOCUMENTS

| | | | |
|---|---|---|---|
| 2,876,770 | 3/1959 | White | 604/232 X |
| 4,573,976 | 3/1986 | Sampson et al. | 604/198 |
| 4,767,413 | 8/1988 | Haber et al. | 604/232 X |
| 4,915,701 | 4/1970 | Halkyard | 604/232 X |
| 4,931,040 | 6/1990 | Haber et al. | 604/232 X |

Primary Examiner—John D. Yasko
Attorney, Agent, or Firm—Leon Gilden

[57] ABSTRACT

A syringe construction for use particularly in dental procedures, wherein the syringe includes an outer tubular body with a forward cap mounted thereon. A shield of arcuate configuration coaxially aligned relative to the tubular body and projecting through a slot in the forward cap is telescopingly mounted relative to the tubular body for effecting shielding of an associated needle mounted by the syringe for minimizing trauma and inadvertent injury of the needle relative to an associated dental patient.

6 Claims, 6 Drawing Sheets

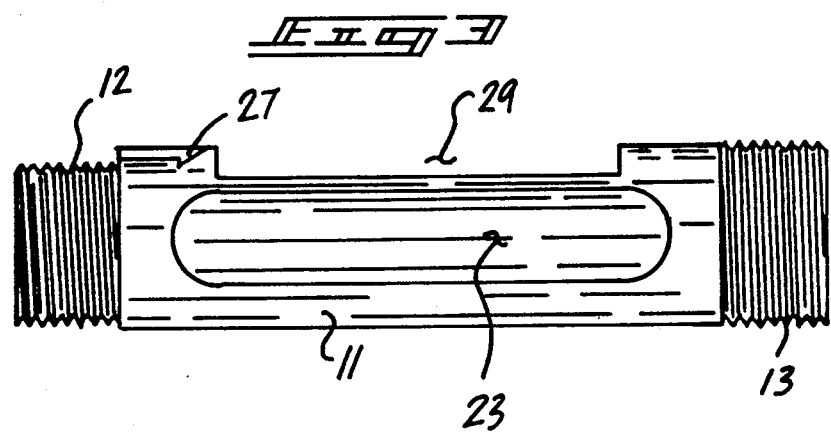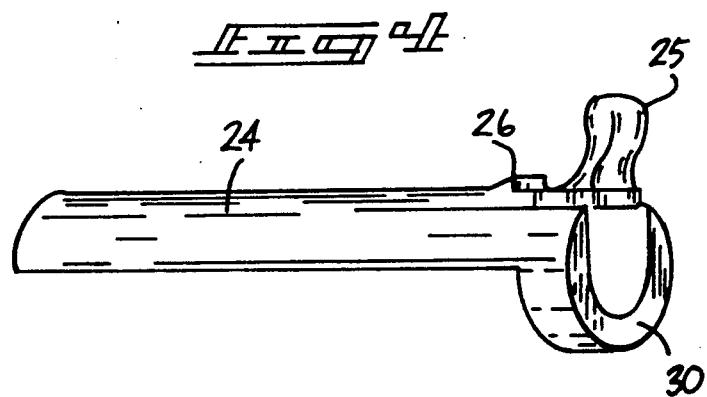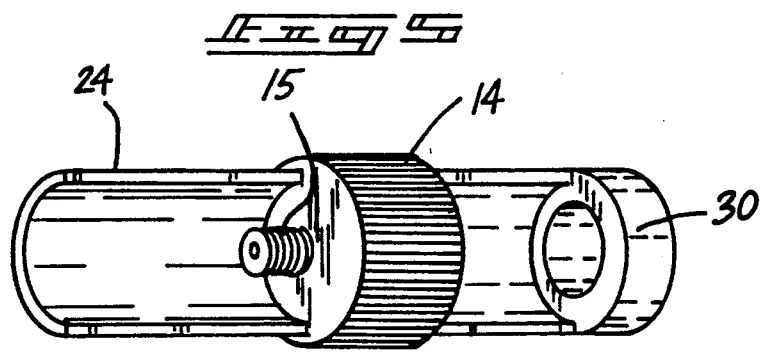

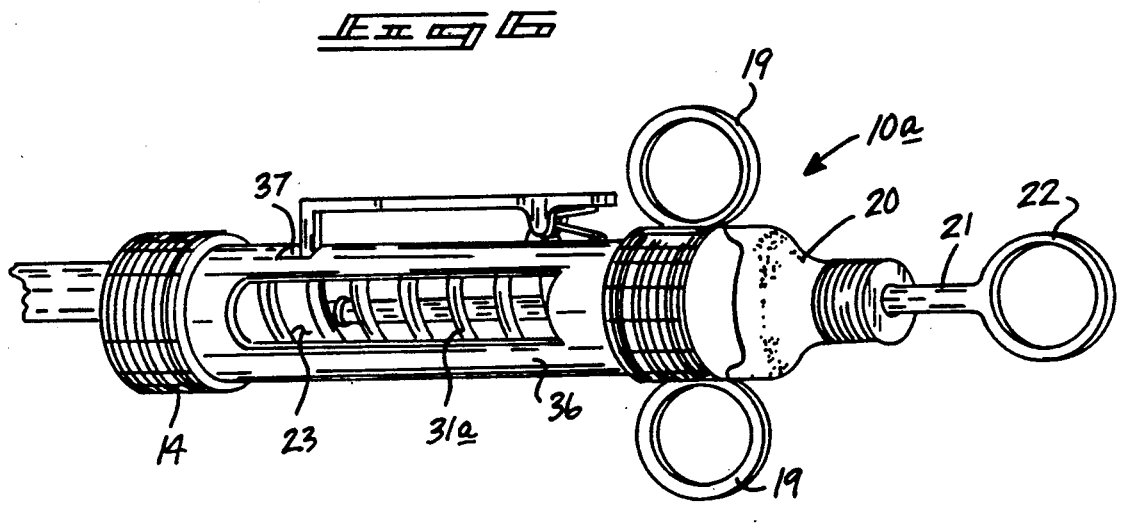
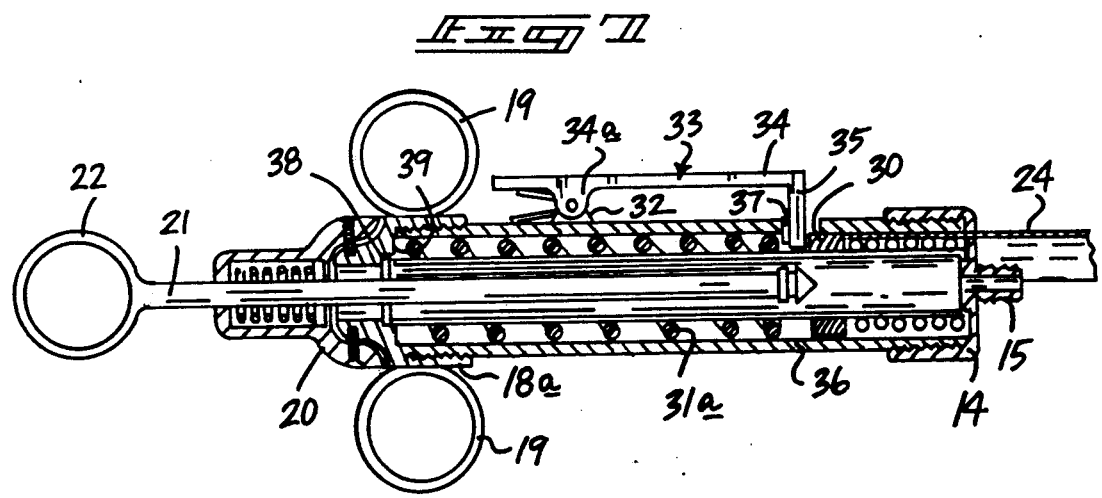

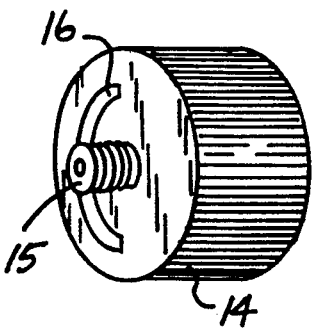
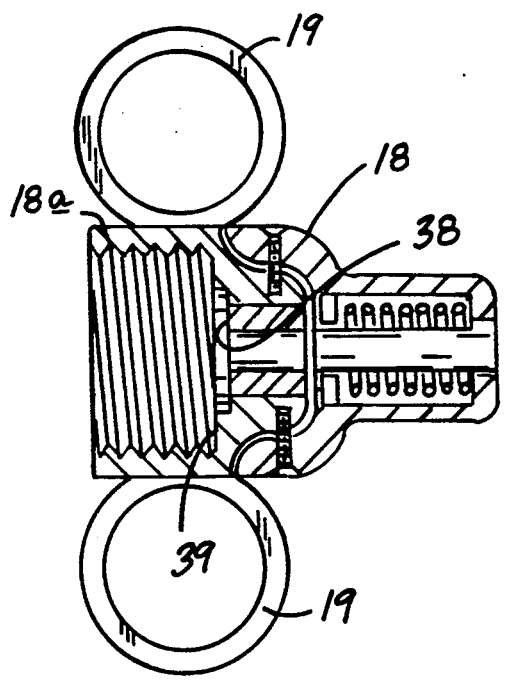
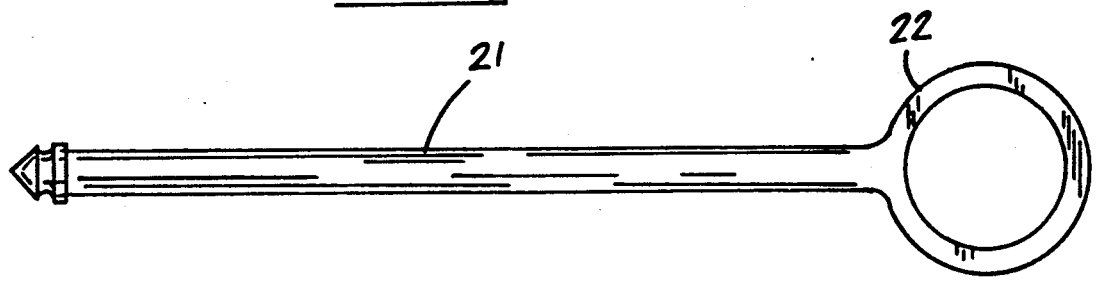

DENTAL SYRINGE APPARATUS

BACKGROUND OF THE INVENTION

1. Field of the Invention

The field of invention relates to syringe apparatus, and more particularly pertains to a new and improved dental syringe apparatus wherein the same is arranged for providing a shield construction for selective use in cooperation with a needle mounted on the syringe.

2. Description of the Prior Art

In dental procedures, the configuration size and use of a dental syringe in a typical sensitive oral area of a patient is frequently associated with emotional trauma, as well as an ever present danger of inadvertent injury to a patient or dental practitioner. The instant invention attempts to overcome deficiencies of the prior art by providing a shield structure arranged for direction to overlie the needle, wherein the shield is coaxially mounted relative to the syringe body and directed telescopingly relative to the body in use. Examples of prior art may be found in U.S. Pat. No. 4,911,693 to Paris wherein a tubular shield projects in surrounding relationship relative to the needle, but prevents the use of a needle portion when the shield is an extended configuration.

U.S. Pat. No. 4,915,697 to Dupont sets forth a hypodermic needle assembly wherein the needle member is mounted within a housing prior to its use.

U.S. Pat. No. 4,921,490 to Spier, et al. sets forth a needle structure mounting a selectively removable casing thereabout.

U.S. Pat. No. 4,867,712 to Haber, et al. sets forth a needle member wherein a collapsing cover surrounds the forward or distal end of the needle prior use.

U.S. Pat. No. 4,850,996 to Cree sets forth a further example of a needle structure utilizing a surrounding housing.

As such, it may be appreciated that there continues to be a need for a new and improved dental syringe apparatus as set forth by the instant invention which addresses both the problems of ease of use as well as effectiveness in construction utilizing a shield permitting simultaneous use of the shield and the associated needle structure and in this respect, the present invention substantially fulfills this need.

SUMMARY OF THE INVENTION

In view of the foregoing disadvantages inherent in the known types of syringe apparatus now present in the prior art, the present invention provides a dental syringe apparatus wherein the same is arranged for telescopingly mounting an arcuate shield to project the shield to overlie the associated needle permitting access of the needle to various portions of an oral region of a patient. As such, the general purpose of the present invention, which will be described subsequently in greater detail, is to provide a new and improved dental syringe apparatus which has all the advantages of the prior art syringe apparatus and none of the disadvantages.

To attain this, the present invention provides a syringe construction for use in dental procedures, wherein the syringe includes an outer tubular body with a forward cap mounted thereon. A shield of arcuate configuration coaxially aligned relative to the tubular body and projecting through a slot in the forward cap is telescopingly mounted relative to the tubular body for effecting shielding of an associated needle mounted by the syringe for minimizing trauma and inadvertent injury of the needle relative to an associated dental patient.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved dental syringe apparatus which has all the advantages of the prior art syringe apparatus and none of the disadvantages.

It is another object of the present invention to provide a new and improved dental syringe apparatus which may be easily and efficiently manufactured and marketed.

It is a further object of the present invention to provide a new and improved dental syringe apparatus which is of a durable and reliable construction.

An even further object of the present invention is to provide a new and improved dental syringe apparatus which is susceptible of a low cost of manufacture with regard to both materials and labor, and which accordingly is then susceptible of low prices of sale to the consuming public, thereby making such dental syringe apparatus economically available to the buying public.

Still yet another object of the present invention is to provide a new and improved dental syringe apparatus which provides in the apparatuses and methods of the prior art some of the advantages thereof, while simultaneously overcoming some of the disadvantages normally associated therewith.

Still another object of the present invention is to provide a new and improved dental syringe apparatus wherein the same is arranged for telescopingly directing an arcuate shield to overlie a needle member creating access of the needle for injection while simultaneously minimizing visual observation of the needle in use.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an orthographic side view of the external tubular body utilized by the instant invention.

FIG. 4 is an isometric illustration of the arcuate shield utilized by the instant invention.

FIG. 5 is an isometric illustration of the arcuate shield in cooperation with the forward cap utilized by the instant invention.

FIG. 6 is an isometric illustration of a modified configuration of the instant invention.

FIG. 7 is an orthographic side view of the modified syringe construction as set forth in FIG. 6.

FIG. 14 is an isometric illustration of the forward cap utilized by the instant invention.

FIG. 15 is an orthographic side view of the end cap utilized by the instant invention.

FIG. 16 is an orthographic side view of the plunger utilized by the instant invention.

DESCRIPTION OF THE PREFERRED EMBODIMENT

Figure 1:
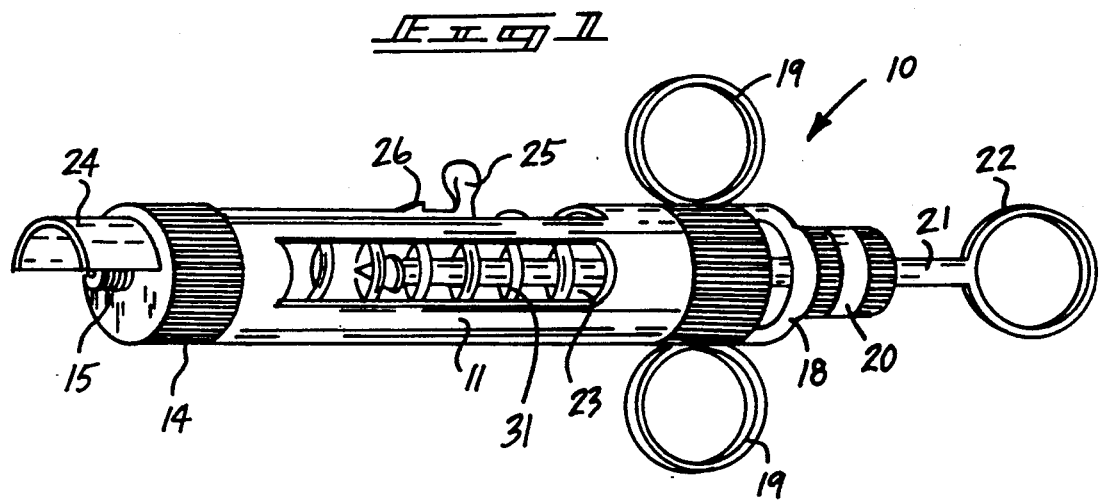
FIG. 1 is an isometric illustration of the instant invention.
Figure 2:
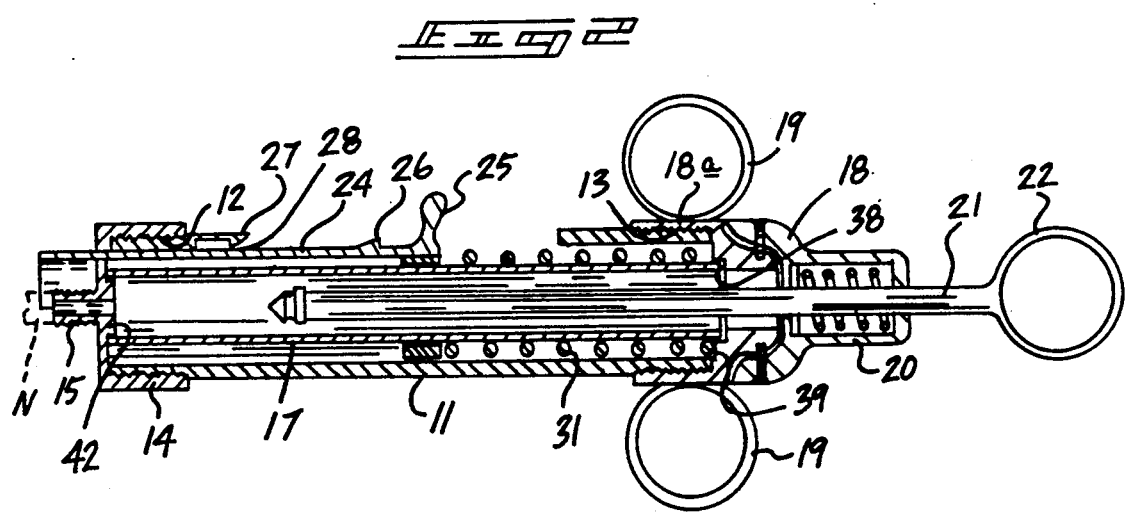
FIG. 2 is an orthographic cross-sectional illustration of the instant invention.
Figure 17:
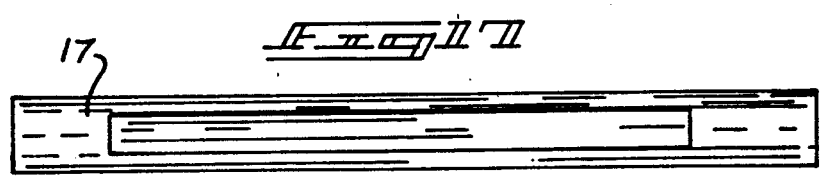
FIG. 17 is an orthographic side view of the internal tubular body utilized by the instant invention.
Figure 8:
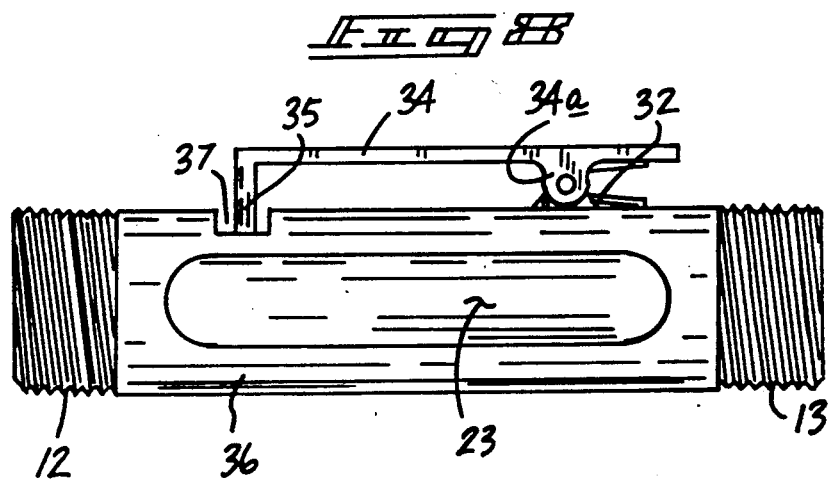
FIG. 8 is an orthographic side view of the modified syringe apparatus of the instant invention.
Figure 9:
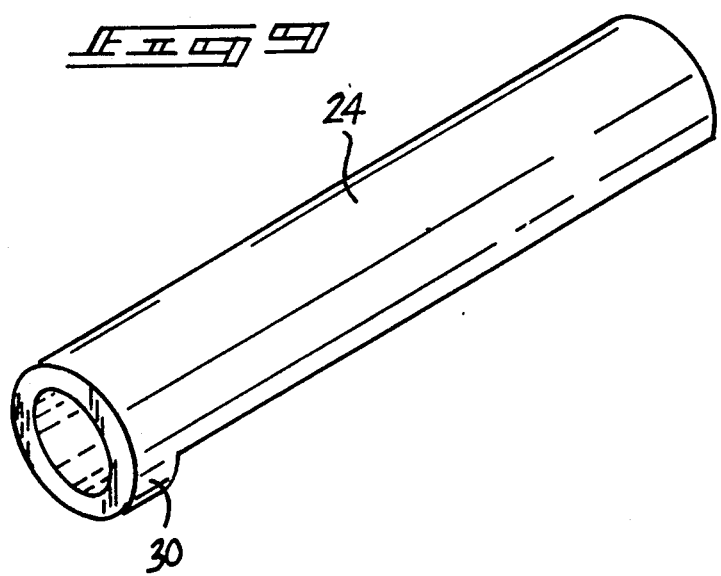
FIG. 9 is an isometric top view of the arcuate shield construction utilized by the modified syringe apparatus.
Figure 10:
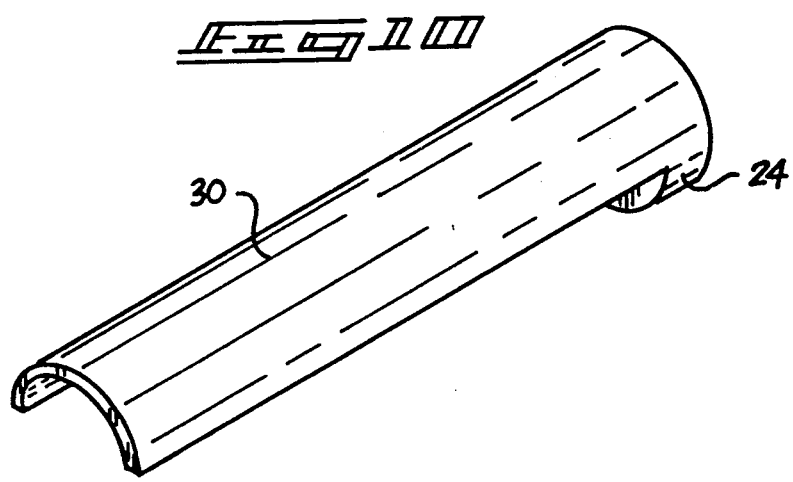
FIG. 10 is an orthographic frontal view of the shield construction utilized by the modified syringe apparatus.
Figure 11:
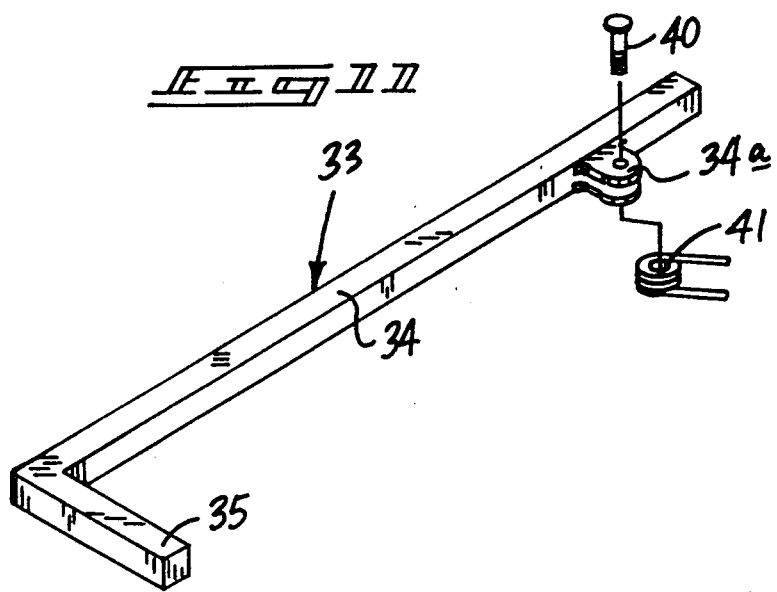
FIG. 11 is an isometric illustration of the locking lever utilized by the instant invention.
Figure 12:
FIG. 12 is an orthographic side view of a first extension spring utilized by the instant invention mounted between the internal and external tubular bodies.
Figure 13:
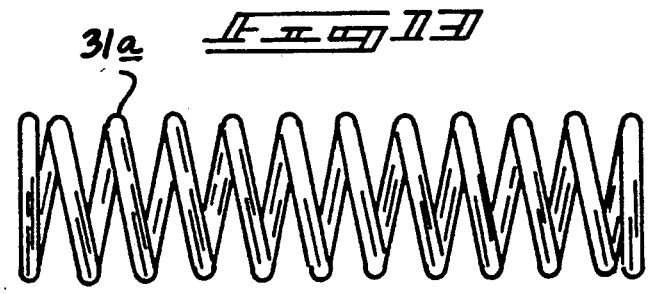
FIG. 13 is an orthographic side view of the modified spring utilized by a modified syringe apparatus positioned between the external and internal tubular bodies.

With reference now to the drawings, and in particular to FIGS. 1 to 17 thereof, a new and improved dental syringe apparatus embodying the principles and concepts of the present invention and generally designated by the reference numerals 10 and 10a will be described.

More specifically, the dental syringe apparatus of the instant invention essentially comprises an external tubular body 11, including an externally threaded forward portion 12 and an externally threaded rear portion 13. The tubular body 11 removably mounts to the externally threaded forward portion 12 a forward cap 14 that includes an internally threaded skirt securable to the forward portion 12, with an externally threaded needle support base 15 formed with a central bore to threadedly receive a conventional hypodermic needle thereon. The forward cap 14 includes an arcuate slot 16 whose axis is coincident with the central bore of the needle support boss 15 and the tubular body 11 (see FIG. 14). An internal tubular body 17 is coaxially mounted within the external tubular body 11 to receive a capsule for injection of fluid through the needle support boss 15. A plunger 21 coaxially aligned relative to the internal and external tubular bodies projects the capsule in a conventional manner through the threaded boss 15. The rear cap 18, including an internally threaded rear cap skirt 18a, is threadedly received on the externally threaded rear portion 13, including a support body 20 to mount the plunger 21 coaxially relative to the end cap and internal and external tubular bodies. A plurality of diametrically opposed cylindrical rings 19 are fixedly mounted to opposed sides of the rear cap skirt 18a to permit a forefinger and index finger to be directed therethrough in cooperation with a thumb directed through the plunger ring 22 mounted to a rear terminal end of the plunger 21. A window slot 23 directed through the external tubular body 11 permits visual observation of components and their cooperation, as well as the relative contents of medicine contained within the internal tubular 17. Typically, the various components of the organization are formed of titanium or stainless steel and the like for use in a dental environment. An arcuate shield is slidably mounted and received within a relief slot 29 formed within the tubular body 11. The arcuate shield 24 is slidably received through the arcuate slot 16 and is telescopingly mounted in a sliding relationship relative to the external tubular body 11. The arcuate shield 24 is defined by a generally semi-cylindrical configuration complementary to that of the arcuate slot 16. An engagement flange 25 is mounted orthogonally relative to a rear terminal end of the arcuate shield 24, and a shield lock projection 26 is mounted adjacent the flange 25 and is receivable within a shield lock flange 27 mounted to the external tubular body 11 adjacent to a rear terminal end of the externally threaded forward portion 12 and defines an access slot 28 that is aligned with the lock projection 26 to selectively receive the lock projection 26 and effectively lock the shield in a forward position. A shield mounting ring 30 slidingly and surroundingly is mounted about the internal tubular body 17 to coaxially align the shield relative to its sliding movement relative to the external tubular body 11, wherein the coil spring 31 is captured between a rear surface of the shield mounting ring 30 and is seated upon a cylindrical body spring mounting surface 39 formed on a forward end of the rear cap 18, wherein the spring mounting surface 39 is orthogonally oriented relative to the axis of the external tubular body 11 and the plunger 21. A support body cylindrical recess 38 is formed medially of the spring mounting surface 39 to secure the rear terminal end of the internal tubular body 17 in a desired relationship. The relationship may be of a threaded intercommunication, or merely of a press-fit configuration, as illustrated. A forward cap boss 42 is coaxially mounted to an internal surface of the forward cap in surrounding relationship relative to the bore of the support boss 15 and defined by an external diameter substantially equal to an internal diameter defined by the internal tubular body 17 to align the internal tubular body 17 to the forward cap boss 42 and the forward cap 14.

FIGS. 6 and 7 exemplify a modified dental syringe apparatus 10a, wherein an "L" shaped lock lever 33 is mounted to an exterior surface of a modified external tubular body 36, wherein the pivot boss 32 pivotally mounts an "L" shaped lock lever 33. The "L" shaped lock lever 33 includes a first leg 34, with a second leg 35 fixedly and orthogonally mounted to a forward terminal end of the first leg 34. The first leg 34 includes a first leg pivot boss 34a cooperative with the pivot boss 32 utilizing a first leg axle 40 to pivotally mount the first leg 34 to the pivot boss 32, with a biasing spring 41 captured between the first leg 34 and the exterior surface of the modified external tubular body 36 (see FIGS. 7 and 11 for example). The arcuate shield 24 includes the shield mounting ring 30 at a rear terminal end thereof in sliding engagement relative to the internal tubular body 17 in a manner as discussed above, wherein a modified coil spring 31 is captured between a rear surface of the mounting ring 30 and the spring mounting surface 39. In a retracted configuration, a forward end of the shield 24 is in abutment with the second leg 35 that projects through the modified tubular body 36 through a second leg receiving slot 37 formed within the tubular body 36. Upon depressing of the first leg 34 rearwardly of the pivot boss 32, the second leg 35 is withdrawn from the receiving slot 37 permitting instantaneous projection of the shield 24 to extend over the needle support boss 15 and an associated hypodermic needle mounted thereon.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A dental syringe apparatus comprising, in combination,
   an elongate external tubular body, the tubular body including a forward end portion and a rear end portion, the forward end portion mounting a forward cap thereon, the forward cap including an externally threaded needle support base, with the needle support base including a central bore directed therethrough, with the central bore coaxially aligned with the external tubular body,
   the forward cap including an arcuate slot directed through the forward cap, with the arcuate slot defined within a predetermined circle, with the central bore defining a predetermined axial center of the predetermined circle, and
   a cap mounted to the rear end portion of the tubular body, and
   an internal tubular body coaxially aligned with the external tubular body coextensive therewith and mounted between the forward cap and the rear cap, and
   an arcuate shield member reciprocatingly mounted through the arcuate slot and slidably mounted between the external tubular body and the internal tubular body.

2. An apparatus as set forth in claim 1 wherein the arcuate shield includes a mounting ring, with the mounting ring fixedly mounted to a rear terminal end of the arcuate shield and the mounting ring slidably and surroundingly mounted about the internal tubular body.

3. An apparatus as set forth in claim 2 including a coil spring captured between a rear surface of the mounting ring and the rear cap, with the coil spring positioned between the external tubular body and the internal tubular body.

4. An apparatus as set forth in claim 3 including engagement means for permitting projection of the arcuate shield in a first position extending forwardly and beyond the needle support boss.

5. An apparatus as set forth in claim 4 wherein the engagement means includes an "L" shaped lock lever, the "L" shaped lock lever pivotally mounted exteriorly of the tubular body, wherein the "L" shaped lock lever includes a first leg, and the first leg includes a first leg pivot boss, the external tubular body includes a pivot boss cooperative with the first leg pivot boss to pivotally mount the first leg relative to the tubular body, and a second leg mounted at a forward distal end of the first leg, and a receiving slot directed through the external tubular body, with the second leg receivable through the receiving slot and engageable with the arcuate shield to maintain the arcuate shield in a retracted position and wherein the first leg is pivoted relative to the external tubular body to release the arcuate shield to an extended position.

6. An apparatus as set forth in claim 4 wherein the engagement means includes an engagement flange mounted to a rear terminal end of the arcuate shield extending exteriorly of the tubular body, and further including a shield lock projection mounted to an exterior surface of the arcuate shield adjacent the engagement flange, and a shield lock flange mounted to the external tubular body adjacent the forward end portion to the receive the shield lock projection therewithin.

* * * * *